US010987216B2

(12) United States Patent
Vyas et al.

(10) Patent No.: US 10,987,216 B2
(45) Date of Patent: Apr. 27, 2021

(54) PROSTHETIC VALVE

(71) Applicant: Meril Life Sciences Pvt Ltd, Vapi (IN)

(72) Inventors: Rajnikant Gandalal Vyas, Mumbai (IN); Pramod Kumar Minocha, Vapi (IN); Harshad Amrutlal Parmar, Vapi (IN)

( * ) Notice: Subject to any disclaimer, the term of this patent is extended or adjusted under 35 U.S.C. 154(b) by 0 days.

(21) Appl. No.: 16/008,900

(22) Filed: Jun. 14, 2018

(65) Prior Publication Data

US 2018/0289476 A1    Oct. 11, 2018

Related U.S. Application Data

(63) Continuation-in-part of application No. PCT/IN2017/050525, filed on Nov. 11, 2017, and a continuation-in-part of application No. PCT/IB2016/057642, filed on Dec. 15, 2016.

(30) Foreign Application Priority Data

Dec. 15, 2015   (IN) .......................... 4699/MUM/2015
Sep. 28, 2017   (IN) .............................. 201723034538

(51) Int. Cl.
    *A61F 2/24*    (2006.01)
(52) U.S. Cl.
    CPC ............ *A61F 2/2418* (2013.01); *A61F 2/243* (2013.01); *A61F 2/2433* (2013.01); *A61F 2220/0075* (2013.01); *A61F 2230/0054* (2013.01); *A61F 2250/0039* (2013.01); *A61F 2250/0097* (2013.01); *A61F 2250/0098* (2013.01)

(58) Field of Classification Search
    CPC ....................................................... A61F 2/24
    See application file for complete search history.

(56) References Cited

U.S. PATENT DOCUMENTS 7,993,394 B2    8/2011 Hariton et al.
2011/0238168 A1*   9/2011 Pellegrini ............ A61F 2/2412
                                                        623/2.17

\* cited by examiner

*Primary Examiner* — Matthew W Schall

(57) ABSTRACT

A prosthetic valve has fluoroscopic properties for precise placement of the prosthetic valve in a human stenosed aortic orifice. The prosthetic valve comprises a support frame having a distal and a proximal end, and three adjacently placed rows of hexagonal cells (namely an upper, middle and a lower row). The upper row occupies 50-55% of total length of the support frame. The support frame of the prosthetic valve under fluoroscopy comprises a plurality of light bands and dark bands alternating with each other along the length of the support frame. Further, a second dark band from the distal end of the support frame is bisected by aortic annular plane on placement in orthotopic position of a human stenosed aortic orifice. The prosthetic valve offers advantages such as minimal protrusion in left ventricle and minimal obstruction of prosthetic valve to ostia of coronary arteries.

10 Claims, 9 Drawing Sheets

PROSTHETIC VALVE

CROSS-REFERENCE TO RELATED APPLICATIONS

This application is a Continuation-in-Part (CIP) of parent International Application No. PCT/IB2016/057642, filed Dec. 15, 2016, which claims priority to Indian application 4699/MUM/2015, filed Dec. 15, 2015; and a CIP of parent International Application No. PCT/IN2017/050525, filed Nov. 11, 2017, which claims priority to Indian application 201723034538, filed on Sep. 28, 2017. The entire disclosure of each prior application is incorporated by reference herein in its entirety.

FIELD OF THE INVENTION

The present disclosure relates to a prosthetic valve. More specifically, the present invention relates to a prosthetic cardiac valve to be implanted by percutaneous catheterization technique.

BACKGROUND

The human heart is a hollow organ with four chambers separated by respective valves (the aortic, pulmonary, tricuspid and mitral valves). These valves open and close in cyclic rhythm in response to the pressure gradient created by contraction and relaxation of the four chambers to make the blood flow in specific direction. These valves are composed of leaflets (cusps) attached to an annulus. Thus, the native heart valves with the help of leaflets serve critical function in assuring the forward flow and adequate supply of the blood.

The valves of the human heart can suffer from various diseases which result in malfunctioning of the heart causing serious cardiovascular compromise or death. The diseased heart valve may be stenotic and/or incompetent. A stenotic valve is not able to open sufficiently to allow adequate blood flow through it. An incompetent valve is not able to close completely causing blood to flow backwards in quantities more than that in a normally functioning valve.

Surgical techniques are used to repair the diseased valves or replace them with prosthetic valves. Repair of the valve is less drastic than replacement. In a valve replacement surgery, the leaflets of the native valve are excised and the annulus is sculpted to receive a prosthetic valve. Prosthetic valves have been used for many years to replace diseased valves. For many years, the definitive treatment for such disorders is open heart surgery, but such surgeries are prone to many complications. Some patients do not survive the surgical procedure due to the trauma associated with the procedure and duration of extracorporeal blood circulation. Due to this, a number of patients are deemed inoperable and hence remain untreated.

More recently, a percutaneous catheterization technique has been developed for introducing and implanting a prosthetic heart valve using a flexible catheter in a manner that is considerably less invasive than open heart surgery. In this technique, a prosthetic valve is mounted by crimping at the distal end of a flexible catheter. The catheter is introduced into a blood vessel (such as a femoral or carotid artery) of the patient and advanced through the blood vessel till the crimped valve reaches the implantation site. The valve is allowed to expand to its functional size at the site of the defective native valve by inflating a balloon on which the valve has been mounted. Alternatively, in accordance with another method, the valve may have a self-expanding stent or support frame that expands the valve to its functional size by withdrawing the restricting sheath mounted over the valve. The former prosthetic valve is termed as "balloon expandable" and the latter as "self-expanding".

Aortic stenosis is a disease of the aortic valve and it is a very common disease in persons above 70 years of age. The diseased valve is not capable of opening to its full extent during systole and hence free ejection of blood from left ventricle cannot occur. Surgical risk may increase in the patients who are older than 80 years. Treatment of such patients is done by valve implantation by catheterization technique using balloon expandable or self-expanding aortic valve prosthesis.

Either of the balloon expandable and self-expandable valves incorporates a support frame or a stent that is typically a tubular scaffold structure and a plurality of leaflets; typically three leaflets.

The design of the support frame plays important role in the performance of the prosthetic valve. The frame design can make impact on important clinical aspects. Frame can be designed to achieve reduction in profile of the crimped valve, help the physician/operator in optimal placement of the valve at the implant site, reduce protrusion (deep throating) in left ventricle and at the same time avoid obstruction to the coronary ostia which are located close to the native aortic valve etc.

The ideal location of implantation of a prosthetic valve in aorta is the orthotopic position where the attempt is to superimpose the leaflets of the prosthetic valve on the leaflets of the native diseased valve of the patient. Accurate placement and precise deployment of a prosthetic valve in aorta is very important to achieve optimal performance and offers various advantages.

The accurate placement results in better fixation of the prosthetic valve. The annulus of the native valve and its leaflets are stenosed and may also be calcified. When the prosthetic valve is expanded at the orthotopic position, the frame is held firmly within the stenosed annulus which may have calcified leaflets, thereby offering geographical fix which eliminates risk of embolization of the prosthetic valve by dislodgement.

The second advantage is minimal protrusion of valve in left ventricle. It is important to deploy prosthetic valve at its annular position and not too deep towards ventricular end, also known as infra-annular position due to two important sub-aortic anatomical zones. First zone being the left ventricular outflow tract (LVOT) which has densely populated cardiac conduction musculature which carry electrical impulses to maintain normal heart rhythm. It is important that the prosthetic valve does not herniate into the LVOT thereby not disturbing cardiac conduction system. The second zone being the aorto-mitral continuity and position of native mitral valve which is located in posterio-laterally to the aortic valve. Wrongly positioned prosthetic valve will have the propensity to interfere with normal functioning of the anterior leaflet of the mitral valve, thus impacting the functioning of the mitral valve.

The third advantage is minimizing obstruction to ostia of coronary arteries which are located along the coronary sinus of valsalva or may be above the sino-tubular junction. Ideally, the prosthetic valve should not obstruct the blood flow into these arteries by obstructing or causing 'jailing' of their ostia. The precise location of the prosthetic valve at orthotopic position prevents such obstruction by minimizing the protrusion of the frame into the ascending aorta.

SUMMARY

The present invention discloses a balloon expandable prosthetic valve with fluoroscopic properties for implantation in a human stenosed aortic orifice by locating it precisely at the orthotopic position using aortic annular plane as reference. The prosthetic valve comprises a flexible support frame which can expand and contract has a plurality of leaflets, preferentially three leaflets, formed from an animal tissue and annular skirt made from fabric attached to the support frame.

The support frame of the prosthetic valve of the present invention has a distal end and a proximal end; and a plurality of adjacently placed rows of hexagonal cells between the distal end and the proximal end. Each hexagonal cell has a plurality of straight strut members and a plurality of v-shaped strut members. The dimensions of a row may be same as or different than other rows. The prosthetic valve of this embodiment, when placed inside a human aortic orifice in crimped condition and viewed under fluoroscopy, the support frame exhibits a plurality of light bands and dark bands alternating with each other along the length of the support frame. The placement of the valve precisely at orthotopic position is achieved by using aortic annular plane as reference with respect to a specific band under fluoroscopy. The foregoing is explained further by an exemplary embodiment described below.

The support frame of one exemplary embodiment of the prosthetic valve of the present invention has a distal end and a proximal end; and three adjacently placed rows of hexagonal cells between the distal end and the proximal end. The three rows include an upper row, a middle row and a lower row. Each hexagonal cell has a plurality of straight strut members and a plurality of v-shaped strut members. The upper row occupies 50-55% of total length of the support frame. The lower row is towards distal end of the support frame.

The prosthetic valve of this embodiment, when placed inside a human aortic orifice in crimped condition with distal end of the frame towards left ventricle and viewed under fluoroscopy, exhibits three light bands and four dark bands alternating with each other along the length of the support frame. A second dark band of the four dark bands from a distal end of the support frame is virtually bisected by aortic annular plane when the prosthetic valve is positioned at orthotopic position of the human aortic orifice, thereby indicating precise position for implantation.

The exemplary embodiment of a prosthetic valve described above has a support frame having three rows of hexagonal cells with specific lengths. The teaching of the present invention, namely, precise placement of the prosthetic valve at orthotopic position under fluoroscopy by locating a band using aortic annular aorta as reference, may be applied to the frame of a prosthetic valve having more than three rows of cells. In such cases, the frame will have a lower row, an upper row and a plurality of rows between the lower row and the upper row. The lower row is towards the distal end of the frame. For example, when the valve in crimped condition (on an expandable member of the delivery catheter) is positioned in the human aortic orifice, a frame with four rows of hexagonal cells will exhibit five dark bands and four light bands under fluoroscopy. Likewise, under similar conditions, a frame with five rows of hexagonal cells will exhibit six dark bands and five light bands. In either case, precise positioning of the crimped valve at orthotopic position may be achieved by positioning a particular light band or a particular dark band with respect to aortic annular plane. In an individual case, the aortic annular plane may either align with an edge of a band or may bisect a band depending on number of rows and lengths of individual rows in a frame. A person skilled in art can work out the number and dimensions of the cells and fix the criteria for precisely locating the valve at orthotopic position using these principles for any frame structure.

The teaching of this invention may be applied to a prosthetic valve frame made of cells that are not hexagonal, provided, this frame structure should exhibit alternate light bands and dark bands under fluoroscopy when the valve is positioned in human aortic orifice.

The present invention also discloses a method for positioning a prosthetic valve in a human aortic orifice at orthotopic position. The method involves crimping the prosthetic valve on a balloon of a delivery catheter. Consequently, the delivery catheter with the crimped prosthetic valve is advanced percutaneously through a patient's vasculature under fluoroscopy, till aortic annular plane of a human stenosed aortic orifice either (a) aligns with one of the edges of one of a dark band or a light band or (b) bisects one of a dark band or a light band as visible under fluoroscopy. Further, the crimped prosthetic valve is parked at this location and is implanted by inflating it.

The foregoing and other features and advantages of the invention will become more apparent from the following detailed description, which proceeds with reference to the accompanying figures.

BRIEF DESCRIPTION OF THE DRAWINGS

The summary above, as well as the following detailed description of illustrative embodiments, is better understood when read in conjunction with the appended figures. For the purpose of illustrating the present disclosure, exemplary constructions of the disclosure are shown in the figures. However, the disclosure is not limited to specific methods and instrumentalities disclosed herein. Moreover, those familiar with the art will understand that the figures are not to scale. Wherever possible, like elements have been indicated by identical numbers.

In the figures and the description to follow, the terms "frame" or "stent" or "frame structure" or "scaffold structure" or "support frame" or "scaffold" refer to the metallic frame of this invention. These terms are used interchangeably but carry the same meaning. The term "valve" or "prosthetic valve" refer to the prosthetic valve of this invention assembled using the frame structure and other components like leaflets of animal tissue, skirt, etc. These terms are also used interchangeably. The term "native valve" is used for the natural valve in human heart.

DETAILED DESCRIPTION

Figure 1:
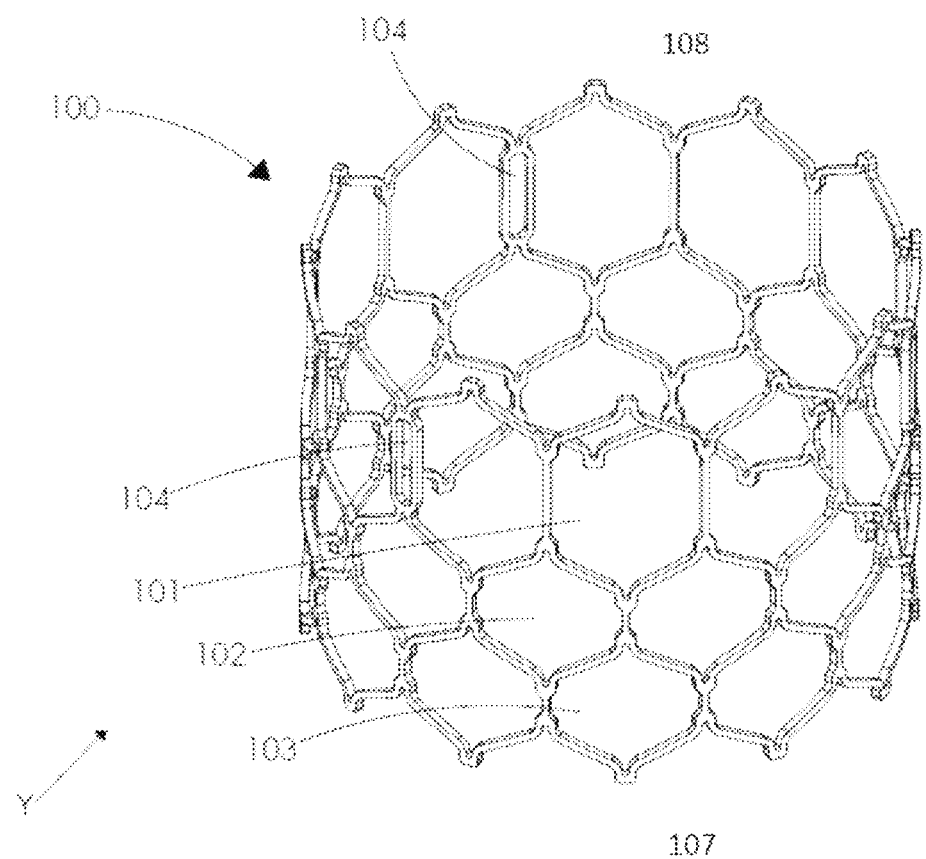
FIG. 1 is a perspective view of the support frame in accordance with an embodiment of the present disclosure.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise.

The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached figures may not show the various ways in which the disclosed system, method, and apparatus can be used in combination with other systems, methods, and apparatuses.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all 25 embodiments. These features and advantages of the embodiments will become more fully apparent from the following description and appended claims, or may be learned by the practice of embodiments as set forth hereinafter.

Disclosed embodiments of an improved radially expandable and compressible support frame having a plurality of leaflets made of animal tissue can be used with any prosthetic valve, such as a prosthetic aortic heart valve. The prosthetic valve with the embodiments of the support frame offers many advantages as described further.

The terms "upper", "middle", "lower", "vertical" and "horizontal" refer to a specific way an item or a component is shown in a diagram and do not refer to absolute direction or location.

The present invention discloses a balloon expandable prosthetic valve implanted by catheterization technique in a human stenosed aortic orifice.

A representative embodiment of the present disclosure provides a prosthetic valve having a flexible support frame which can expand and collapse, a plurality of leaflets (preferentially three leaflets) formed from animal tissue and an annular skirt made from a fabric attached to the frame. Each leaflet has a rectangular shape portion at one end followed by a semi-circular arc (scallop shape) at the other end and two attachment nodes for attaching the leaflet to commissure posts. The scallop shaped portion is fixed by suturing to lower part of the frame and the skirt.

The design of the support frame helps an operator in positioning and deploying the prosthetic valve in precise orthotopic position by viewing under fluoroscopy during implantation procedure. Moreover, the support frame length is such that the protrusion of the support frame in LVOT after implantation at orthotopic position is limited to maximum 4 mm, preferably around 3.3-3.5 mm. This eliminates any possibility of disturbance of the cardiac muscles which carry electrical signals and interfering with normal functioning of the anterior leaflet of the mitral valve. The total length of the support frame is such that the portion of the support frame extending into the ascending aorta after implantation at orthotopic position and the large open cells in the upper row of the support frame ensure un-jailing of the coronary ostia. The design of the support frame makes the prosthetic valve mechanically stronger to make it possible to reduce the strut thickness to 350 micrometers without compromising mechanical strength (radial strength and fatigue resistance) of the support frame.

Figure 1A:
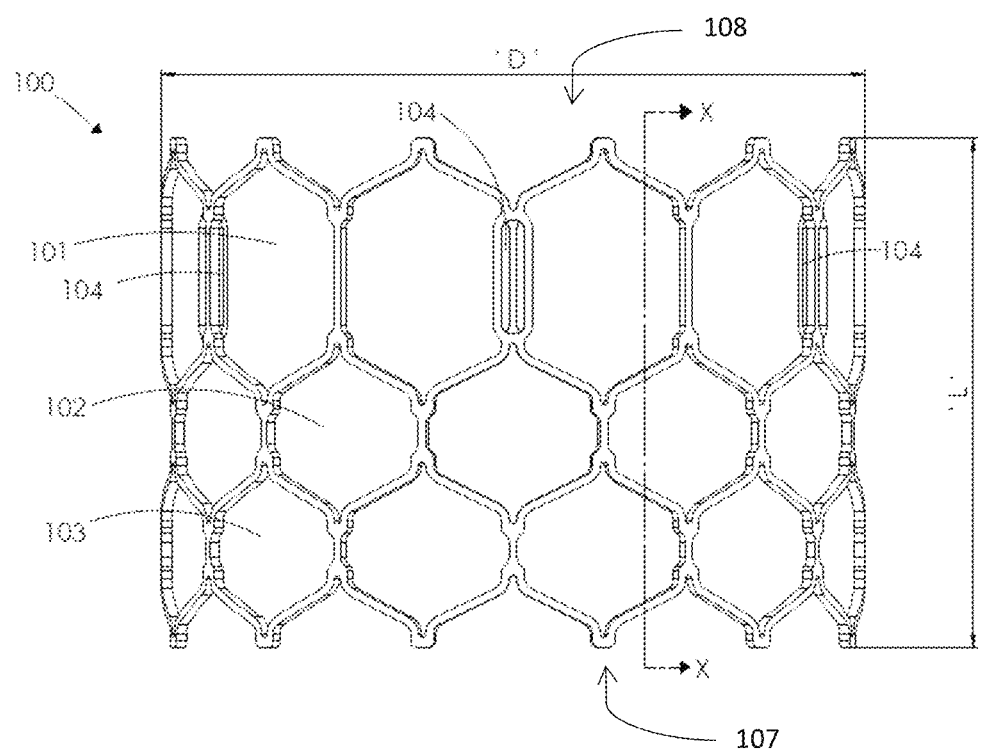
FIG. 1A is the front view of the support frame of FIG. 1 in accordance with an embodiment of the present disclosure.

FIGS. 1 and 1A are embodiments of a support frame 100 of an exemplary embodiment of the prosthetic valve. FIG. 1 is perspective view of the support frame and FIG. 1A depicts front view of the support frame 100 of FIG. 1 when viewed from direction Y. As depicted, the support frame 100 is a cylindrical scaffold structure with diameter D and length L. The support frame 100 has a distal end 107 and a proximal end 108. Further, there are three rows, upper row 101, middle row 102 and lower row 103 of hexagonal cells disposed between the distal and proximal ends 107, 108. The hexagonal cells located in a single row have same cross-sectional area, e.g. cross-sectional area of hexagonal cells located in row 101 is same. However, the cross-sectional area of hexagonal cells located in different rows may be same or different, e.g. cross-sectional area of cells in row 101 may be same or different than the hexagonal cells located in row 102 or row 103. In embodiment, the area of hexagon cells of a row is different than the area of hexagonal cells of one or more of the remaining rows.

The support frame 100 may include a plurality of commissure posts 104 which function to attach one or more leaflets to the support frame 100. As shown in FIG. 1A, there are three commissure posts 104 disposed at 120o with respect to each other located on the upper row 101.

Figure 1B:
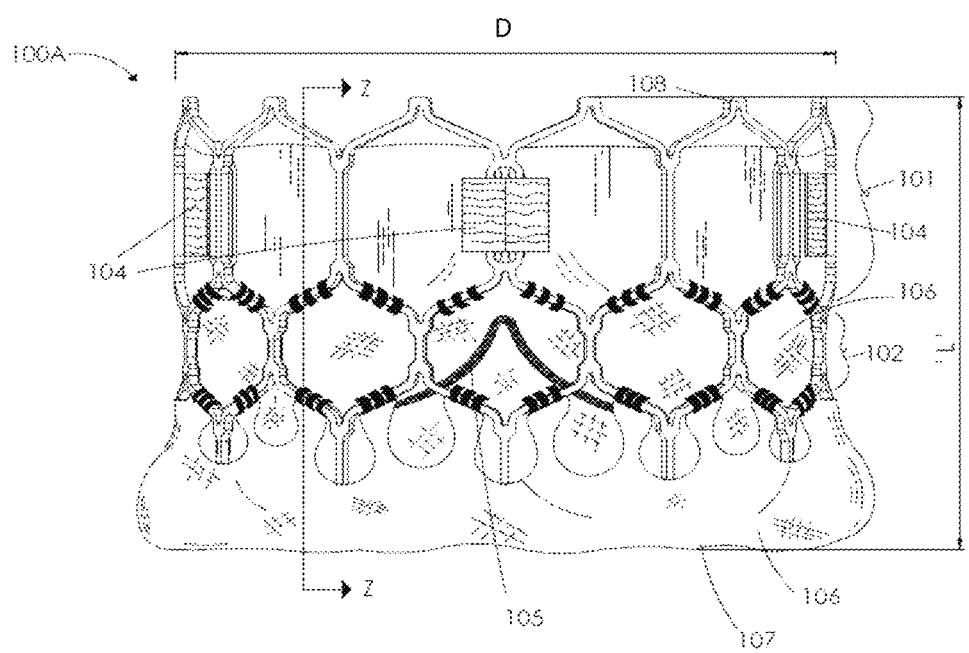
FIG. 1B depicts a prosthetic valve in accordance with an embodiment of the present disclosure.

FIG. 1B depicts the prosthetic valve 100A constructed using the support frame 100 of FIG. 1-1A with diameter D and length L. As depicted in FIG. 1B, there are three commissure posts 104 in the upper row 101 located at 120° to each other. To each of the commissure posts 104, an attachment node of corresponding leaflet is attached. The attachment nodes of two leaflets are sutured to a commissure post 104 of the support frame 100. The scallop portion 105 of the leaflets is attached to the middle row 102 and the lower row 103 by suturing to the cell struts and the skirt 106. Further, a skirt 106 is attached to the support frame covering the middle row 102 and the lower row 103.

The blood enters from the distal end 107 of the prosthetic valve 100A (inflow end) and is discharged through proximal end 108 (outflow end). Hence, after implantation of the prosthetic valve 100A, the lower end 107 is towards the left ventricle and upper end 108 is towards the ascending aorta.

Figure 2:
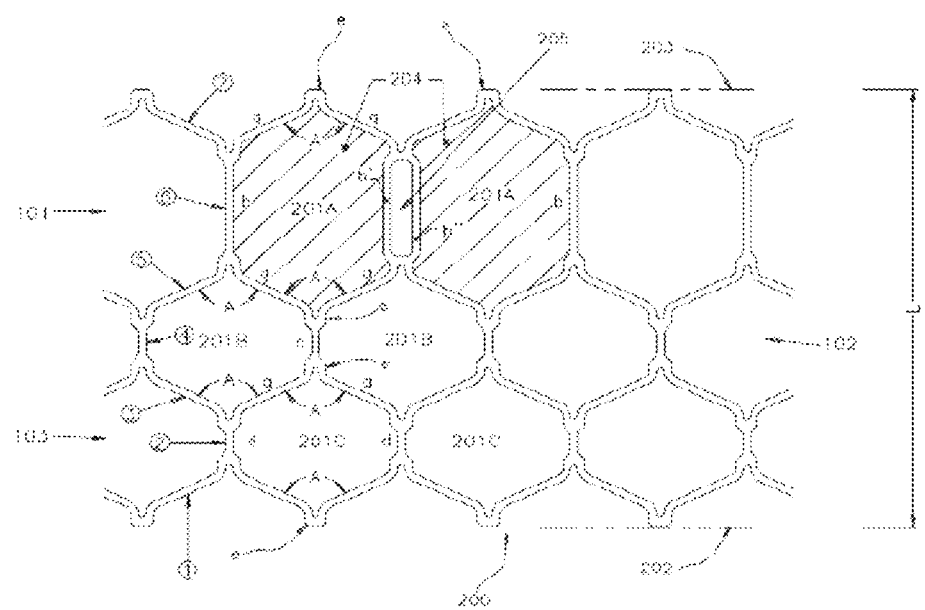
FIG. 2 is a partial view of the cells of the support frame of FIGS. 1 and 1A when the cylindrical frame is cut vertically across its length L and flattened on a plane surface in accordance with an embodiment of the present disclosure.

FIG. 2 depicts an elemental view of a portion of the support frame 100 of FIG. 1-1A 25 when the cylindrical portion of the support frame 100 is cut vertically along its length L (across X-X shown in FIG. 1A) and flattened. This elemental support frame corresponds to a portion of frame 100 and is depicted as 200 in FIG. 2. The support frame 200 comprises a plurality of repetitive strut members a, b, b', b", c and d interconnected to each other to form a scaffold of hexagonal cells. The hexagonal cells are interconnected to yield a honeycomb shaped support frame 100 (FIG. 1-1A). In an embodiment, the support frame 200 has three rows of hexagonal cells viz. upper row 101, middle row 102 and lower row 103 comprising of cells 201A, 201B, and 201C respectively.

The support frame 200 has two ends viz. 202 and 203. The prosthetic valve 100A is structured and implanted in such a manner that the blood follows in at the end 202 and it flows out from end 203. Thus, the end 202 of the support frame 200 is the "inflow end" (corresponding to distal end 107 in FIG. 1/1A/1B) and the end 203 is the "outflow end" (corresponding to proximal end 108 in FIG. 1/1A/1B). After the valve is implanted across the native aortic annulus, the blood will enter the prosthetic valve 100A from end 202 and will leave the valve from the end 203. Hence, the end 202 will be towards the left ventricle and end 203 will be towards the ascending aorta.

Each hexagonal cell 201A, 201B or 201C, as depicted in FIG. 2, has six sides which correspond to six strut members a, b, b', b", c and d. The said sides of cell 201A, 201B or 201C are commonly shared with sides of an adjacent cell 201A, 201B or 201C. As shown in FIG. 2, a strut member 'a' of each cell contains two arms at an angle A that forms a V-shape. The angle A of two arms of the V shaped strut 'a' in each cell may be 120° to 135° (preferably 125° to 130° when the support frame is in fully expanded state. The angle between the two arms of the V shaped struts may be different for different sizes (diameters) of the valves.

The strut members b, b', b", c and d of the hexagonal cells are straight strut members and connect the two pairs of V shaped strut members a. In an embodiment, the lengths of strut members b, b' and b" are same. The lengths of strut members c and d may be same or different. In an embodiment, the strut members b, b' and b" are longer than strut members c and d. These features make the cross-sectional area of cells 201A larger than that of the cells 201B and 201C.

In an embodiment, the cells 201A of the row 101 have strut members 'a' and 'b'. The hexagonal structure of cell 201A has two pairs of V-shaped strut members 'a' and two strut 25 members 'b'. The cells 201A interconnect with each other to form row 101. Two adjacently placed cells 201A share a common strut member b. Each straight strut acting as commissure post (205) is composed of strut members b' and b" in place of a single strut b.

The strut members b' and b" form a rectangular opening 205 in row 101 where the attachment nodes of the leaflets are fixed. In an embodiment, there are three pairs of such b'/b" strut members in the support frame 100 located at 120° to each other forming three commissure posts. Each commissure post has a rectangular opening 205 formed by strut members b' and b". There are methods known in art for attaching the leaflets to such commissure posts.

Similarly, in an embodiment, the cells 201B of the middle row 102 have strut members 'a' and 'c'. The hexagonal structure of cell 201B has two pairs of V-shaped strut members 'a' and two strut members 'c'. The cells 201B interconnect with each other to form row 102. Two adjacently placed cells 201B share a common strut member c.

Likewise, the cells 201C of the lower row 103 have strut members 'a' and 'd'. The hexagonal structure of cell 201C has two pairs of V-shaped strut members 'a' and two strut members 'd'. The cells 201C interconnect with each other to form row 103. Two adjacently placed cells 201C share a common strut member d.

The interconnection points of all the strut members a, b, b', b", c and d are rounded. In an embodiment, for example, two strut members 'a' intersect with each other forming a U shape, shown as "e" in FIG. 2. As is evident in FIG. 2, all points of interconnections are rounded in U shape. This U shape helps to dissipate the excessive stress concentration at these intersection points.

The total length of the support frame 100 of this embodiment is L. In an embodiment, the upper row 101 made of cells 201A occupies around 50%-55%, preferably 52%-53% of the total length of the support frame 100. The middle row 102 and lower row 103 made of cells 201B and 201C together occupy the rest of the length of the support frame 100. Due to this, the cross-sectional area of cells 201A is larger than that of cells 201B or 201C.

The honeycomb structure of support frame 100 makes the frame structure mechanically stronger which makes it possible to reduce the strut thickness without compromising mechanical strength of the support frame viz. its radial strength and fatigue resistance. The low 25 strut thickness results in reduction of the profile of the prosthetic valve 100A when crimped on the balloon of the delivery catheter. The low profile makes it easy to maneuver the crimped valve through patient's vasculature to the target site in aorta. In an embodiment, the support frame 100 is made from a metal alloy, say, Cobalt-Chromium-Molybdenum alloy, for example, MP35N or alloy L605. The thickness of the struts of the support frame 100 of an embodiment, when made from alloy MP35N, is 350 micrometers. The support frame 100 has radial strength of at least 100 Newtons, preferably in the range of 150-200 Newtons. This frame successfully passed durability test for 600 million cycles under conditions specified in ISO 5840.

The cells 201B and 201C are located in the lower half of the support frame structure i.e. towards the inflow end 202 of the prosthetic valve 100A (upstream of the blood flow) and are located towards the left ventricle. The inflow end 202 of the prosthetic valve 100A experiences higher mechanical forces than the outflow end 203 of the prosthetic valve 100A. In an embodiment, the cells 201B and 201C have lower cross sectional area than cells 201A. This results into more dense structure of cells 201B and 201C than cells 201A which imparts higher radial strength to the lower portion of the prosthetic valve 100A to withstand higher mechanical forces at this end.

In an embodiment of the present invention, when implanted in the orthotopic position, the protrusion of the prosthetic valve 100A in LVOT is limited to maximum 4 mm, preferably around 3.3-3.5 mm. This eliminates any possibility of disturbance of the cardiac muscles which carry electrical signals and interfering with normal functioning of the anterior leaflet of the mitral valve.

The overall length L of the prosthetic valve 100A is low and varies from 17 mm to 21 mm (for prosthetic valve 100A with diameter D varying from 20 mm to 29 mm). Lower length helps in eliminating jailing of coronary ostia.

The coronary arteries exit the ascending aorta above the native aortic valve in coronary sinus of valsalva or above sino-tubular junction. These exit ports are termed coronary ostia. The cusps of the native aortic valve are located in such a way that the blood supply to the coronary arteries through these ostia is not obstructed. It is, hence, necessary that a prosthetic valve also does not occlude or jail the coronary ostia and thereby does not obstruct the blood flow into the coronary arteries. On implantation at orthotopic position, the cells 201A would be positioned generally above the native valve i.e. where the coronary ostia are located. As stated above, the length of the support frame 100 is low which ensures that the prosthetic valve 100A does not jail the coronary ostia. In addition, the cells 201A have higher cross sectional area i.e. higher open area (hatched area 204 in FIG. 2). This further ensures that there is no obstruction to the blood flow to the coronary ostia.

It is important that the prosthetic valve 100A is implanted precisely at an optimal location to ensure optimal performance. Ideally, the location of the leaflets (cusps) of a prosthetic valve should be located where the cusps of the native valve are located i.e. at orthotopic location. This is generally achieved by the operator's judgment during implantation under fluoroscopic imaging. The prosthetic valve 100A of the present invention guides the operator to position the prosthetic valve 100A precisely at orthotopic position during implantation.

The prosthetic valve 100A is meant to be mounted on a delivery system catheter by crimping it over the balloon of the delivery catheter. The balloon of this catheter may have three radiopaque markers, one at the distal end, one at the proximal end and one in the center of these two markers. The balloon may have two stoppers on the inner lumen of the catheter. The distance between these stoppers may be such that the prosthetic valve 100A, after crimping, fits precisely between them to ensure a confirmed location of the crimped valve over the balloon.

Figure 3:
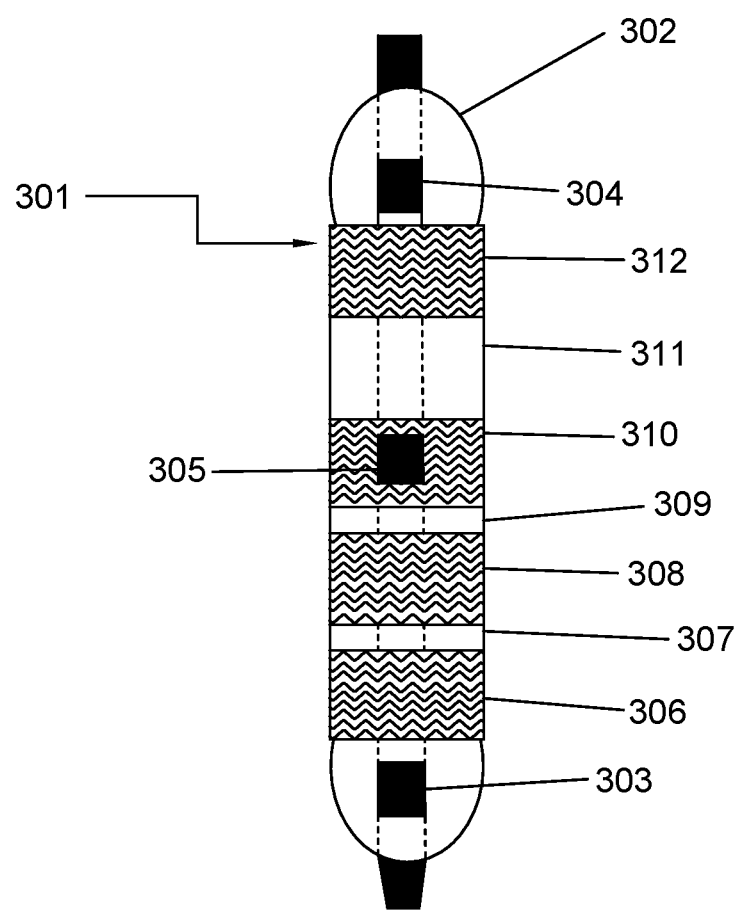
FIG. 3 is a schematic view of the prosthetic valve of FIG. 1B when crimped on the balloon of the delivery system in accordance with an embodiment of the present disclosure.

FIG. 3 illustrates schematically the prosthetic valve 301 after crimping on the balloon 302 of the delivery system. The three radiopaque balloon markers are shown as 303 (distal balloon marker), 304 (proximal balloon marker) and 305 (middle balloon marker). The distal balloon marker 303 is towards the left ventricle. When the prosthetic valve 100A is crimped over the balloon 302, the positions of the radiopaque markers may be as shown in FIG. 3. All the three radiopaque markers 304, 305 and 306 are clearly visible under fluoroscopy during implantation.

In an embodiment, the crimped prosthetic valve 301 exhibits alternate "dark bands" and "light bands" as visualized under fluoroscopy. The zone visible near the distal balloon marker 303 is the first dark band 306. The order of zones is: first dark band 306-first light band 307-second dark band 308-second light band 309-third dark band 310-third light band 311-25 fourth dark band 312. As seen in the FIG. 3, the distal and proximal balloon markers 303 and 304 lie outside the length of the crimped prosthetic valve 301 (i.e. beyond the first dark band 306 and the fourth dark band 312).

The said dark bands are formed as a result of higher density of support frame material aggregated due to crimping of the angled strut members 'a' (V shaped configurations) of the support frame 100. The light bands are formed as a result of lower density of crimped support frame material of the straight strut members b, b', b", c and d. Moreover, the metallic material used for the construction of support frame 100 aids in the visualization of dark bands and light bands. When the crimped prosthetic valve 301 is viewed under fluoroscopy, the strut members 'a' at the lowest end (marked as 1 in FIG. 2) are visible as the first dark band 306 (FIG. 3). The straight strut members in row 103, marked as 2 in FIG. 2 are visible as first light band 307 in FIG. 3. In similar manner strut members 'a' marked as 3 (FIG. 2) are visible as second dark band 308 in FIG. 3. In this way the strut members marked 4, 5, 6 and 7 are visible as second light band 309, third dark band 310, third light band 311 and fourth dark band 312 respectively. In an embodiment of the present invention, the support frame 100 is constructed of Cobalt-Chromium-Molybdenum alloy such as MP35N or alloy L605.

Figure 4:
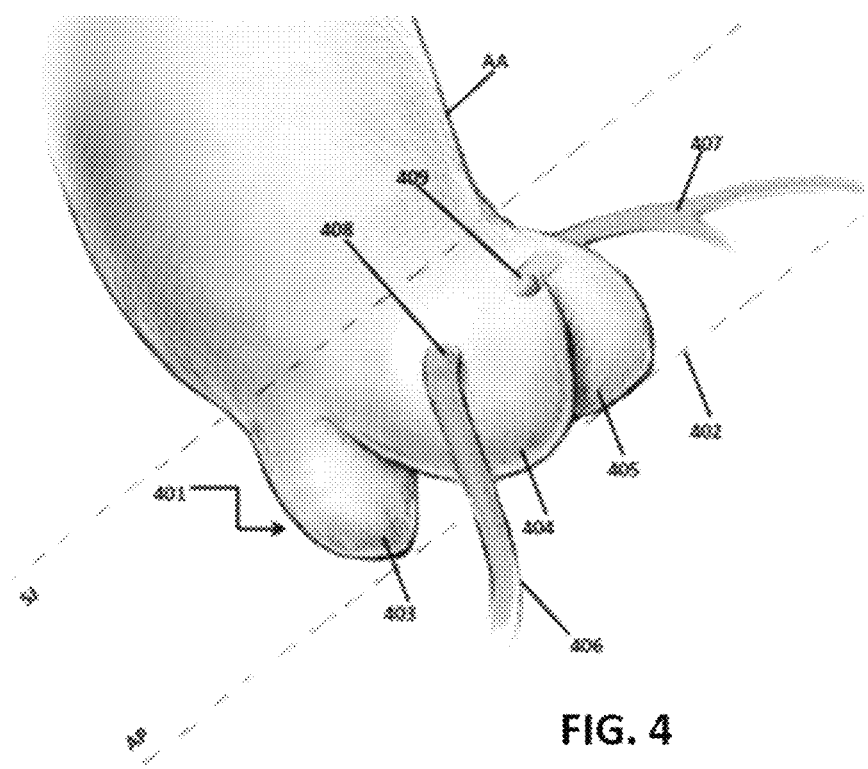
FIG. 4 illustrates the aortic root and annular plane of ascending aorta schematically.

FIG. 4 depicts schematically the aortic root (aortic bulb, 401) of human ascending aorta. Aortic root is the dilated first part of aorta attached to the heart at its end 402. It is a part of the ascending aorta (AA) containing the native aortic valve. The three cusps of the native aortic valve are shown as 403, 404 and 405. The coronary arteries (406 and 407) originate from the vicinity of the aortic bulb 401. The coronary ostia are indicated as 408 and 409. Cusps 404 and 405 are termed "coronary cusps" as coronary arteries 406 and 407 originate at ostia 408 and 409 located in the vicinity of these cusps. The cusp 403 is termed "non-coronary cusp" as no coronary artery originates in the vicinity of this cusp. There are two distinct demarcation planes, one is the aortic Annular Plane (AP) and the second is Sinotubular Junction (SJ). The aortic annular plane AP is clearly visible under fluoroscopy and is a guiding feature to position the prosthetic valve 100A at the orthotopic position for implantation as explained below.

Figure 5:
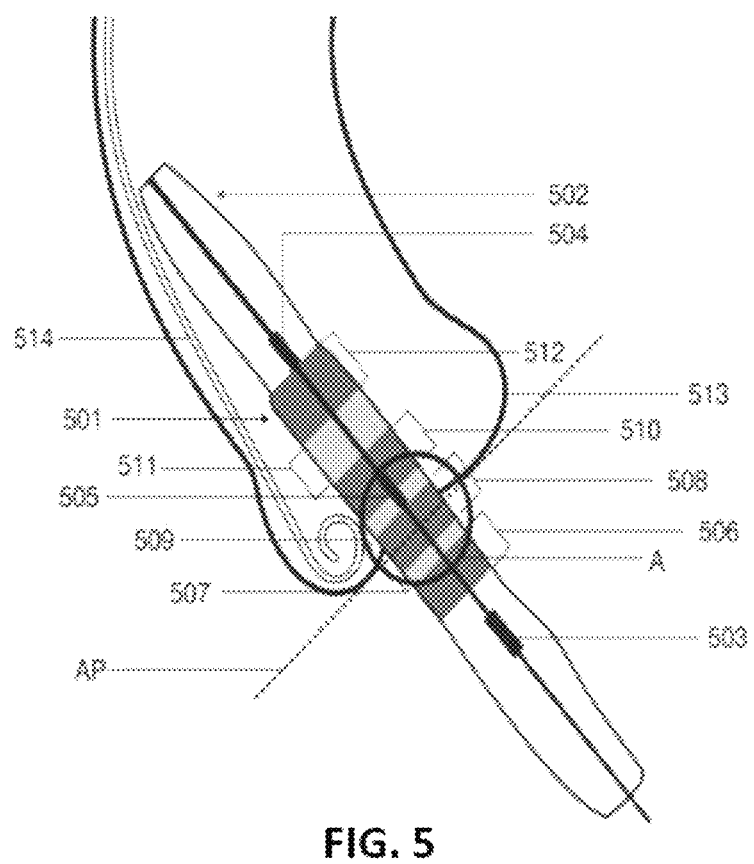
FIG. 5 depicts the schematic view of the crimped prosthetic valve of FIG. 3 when positioned at orthotopic implant location in accordance with an embodiment of the present disclosure.

FIG. 5 shows the prosthetic valve 501 crimped on the balloon 502 of the delivery system when positioned precisely at the orthotopic position for implantation, schematically but representing a fluoroscopy image. The three radiopaque markers are shown as distal balloon marker 503, proximal balloon marker 504 and mid balloon marker 505. Various zones of the crimped prosthetic valve 501 are shown as "The First Dark Band" 506, the "First Light Band" 507, the "Second Dark Band" 508 and the "Second Light Band" 509. Other zones of the crimped prosthetic valve 501 are shown as the "Third Dark Band" 510, the "Third Light Band" 511 and the "Fourth Dark Band" 512. The aortic bulb is shown as 513. The "Annular Plane" is shown as AP. As depicted, the distal balloon marker 503 is towards the left ventricle of the heart.

For percutaneous implantation of a prosthetic valve 100A, a pig-tail catheter 514 is introduced in the heart of a patient and parked at the distal end of the heart in the non-coronary cusp (refer to 403 in FIG. 4). Upon injection of a saline diluted contrast medium through the pig-tail catheter, the aortic root is visible to an operator. The Annular Plane AP (or aortic annular plane) is determined as the virtual line that could be drawn joining the low points of the aortic root. The annular plane AP is a guiding feature to the positioning of the prosthetic valve 100A at precise orthotopic position for implantation.

The catheter with crimped prosthetic valve 501 is navigated through the patient's vasculature to the ascending aorta and is parked at the location where the virtual center line (which bisects the Second Dark Band 508) coincides with the aortic annular plane AP.

Figure 5A:
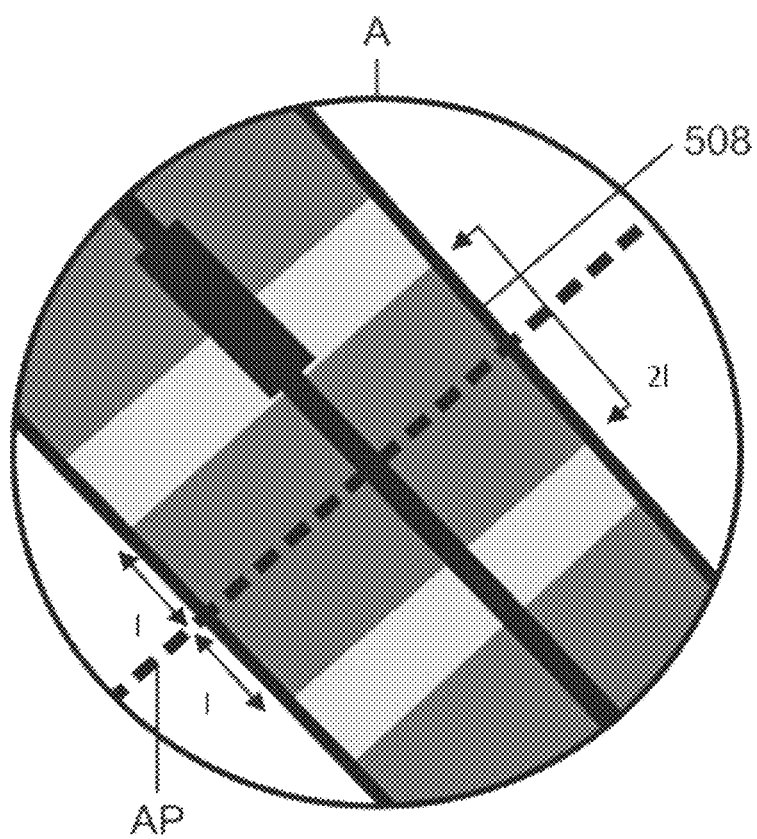
FIG. 5A depicts enlarged view at "A" of the Second Dense Row 508 and the aortic annular plane in accordance with an embodiment of the present disclosure.

This is more clearly depicted in FIG. 5A which is enlarged view at 'A' of FIG. 5. FIG. 5A depicts the Second Dense Row 508 of the crimped prosthetic valve 501 and the virtual line of Aortic Annular Plane AP. AP virtually bisects the Second Dense Band 508. If the total length of the second dense band is 2l, the AP virtually bisects it in two equal halves each of length l. The balloon is then inflated to implant the prosthetic valve 100A at this location.

Figure 6:
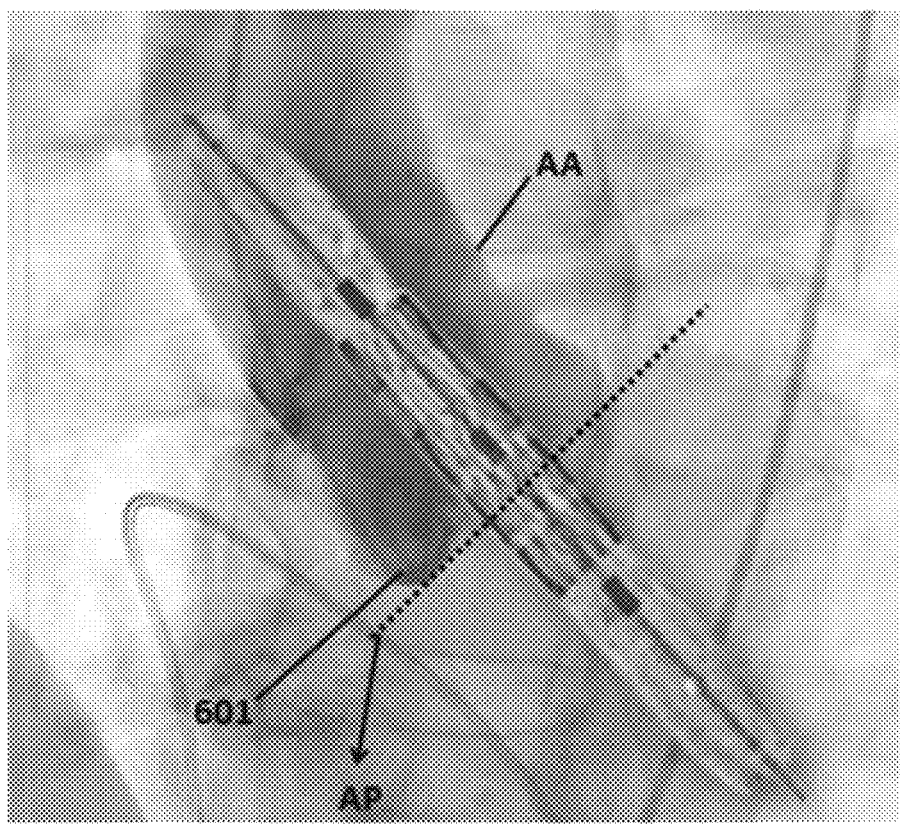
FIG. 6 depicts the crimped prosthetic valve of FIG. 5 as visible in fluoroscopy when positioned at the orthotopic position in accordance with an embodiment of the present 25 disclosure.

FIG. 6 depicts the same view as shown in FIG. 5 but as visible under fluoroscopy when the crimped prosthetic valve 501 is precisely positioned for implantation at orthotopic position. The ascending aorta is shown as AA, aortic bulb as 601 and aortic annular plane as AP as a virtual dotted line. The bisecting line of the Second Dark Band 508 coincides with virtual line of the annular plane AP. All these details are clearly visible to the operator under fluoroscopy to make precise positioning.

The exemplary embodiment of a prosthetic valve described above has a support frame having three rows of hexagonal cells. The teaching of the present invention, namely, precise placement of the prosthetic valve at orthotopic position under fluoroscopy by locating a band using aortic annular aorta as reference, may be applied to the frame of a prosthetic valve having more than three rows of cells. For example, a frame with four rows of hexagonal cells will exhibit five dark bands and four light bands. Similarly, a frame with five rows of hexagonal cells will exhibit six dark bands and five light bands. In either case, precise positioning of the crimped valve at orthotopic position may be achieved by locating a particular light band or a particular dark band with respect to aortic annular plane using the aortic annular plane as reference. In an individual case, the aortic annular plane may align with an edge of a band or may bisect a band depending on number of rows and dimensions of individual rows in a frame. A person skilled in art can work out the number and dimensions of the cells and fix the criteria for precisely locating the valve at orthotopic position using same principles for any frame structure.

The teaching of this invention may also be applied to a prosthetic valve frame made of cells that are not hexagonal, provided, this frame structure should exhibit alternate light bands and dark bands under fluoroscopy when the valve is positioned in human aortic orifice.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims.

What is claimed is:

1. A prosthetic valve with fluoroscopic properties for precise placement of the prosthetic valve in a human aortic orifice, the prosthetic valve comprising:
   a support frame having a distal end, a proximal end and three adjacently placed rows of hexagonal cells between the distal end and the proximal end, the three rows comprising an upper row, a middle row, and a lower row;
      wherein the upper row of hexagonal cells occupies 50-55% of total length of the support frame, and contacts the proximal end of the support frame; and
      wherein the lower row of hexagonal cells is towards the distal end of the support frame;
   wherein each hexagonal cell has a plurality of a) straight strut members and b) v-shaped strut members having two arms;
   wherein the fluoroscopic image of the prosthetic valve, when the prosthetic valve is placed inside a human aortic orifice in crimped condition with the lower row of hexagonal cells towards the ventricle, comprises:
      three light bands; and
      four dark bands, wherein the light bands and the dark bands alternate with each other along the length of the support frame;
      wherein a second dark band of the four dark bands from the distal end of the support frame is bisected by aortic annular plane on placement of the prosthetic valve in orthotopic position of a human aorta.

2. The prosthetic valve as claimed in claim 1, wherein a first cross-sectional area of the hexagonal cells of the upper row is different from a second cross-sectional area of the hexagonal cells of the middle row or the lower row.

3. The prosthetic valve as claimed in claim 1, wherein an angle between the two arms of the v-shaped strut members varies from 125° to 130°.

4. The prosthetic valve as claimed in claim 1, wherein a length of the support frame varies between 17 mm and 21 mm.

5. The prosthetic valve as claimed in claim 1, wherein a diameter of the support frame varies between 20 mm to 29 mm.

6. The prosthetic valve as claimed in claim 1, wherein the support frame is made of a Cobalt-Chromium-Molybdenum alloy, and a thickness of the straight strut members and the v-shaped strut members is 350 micrometers.

7. The prosthetic valve as claimed in claim 6, wherein a radial strength of the support frame is in the range of 150-200 Newtons.

8. The prosthetic valve as claimed in claim 6, wherein a fatigue resistance of the support frame is such as to withstand minimum 600 million cycles under conditions specified in ISO 5840.

9. A prosthetic valve with fluoroscopic properties for precise placement of the prosthetic valve in a human aortic orifice, the prosthetic valve comprising:
   a support frame having a distal end, a proximal end and a plurality of adjacently placed rows of hexagonal cells between the distal end and the proximal end, the plurality of the rows comprising an upper row contacting the proximal end of the support frame, a lower row and a plurality of middle rows between the upper row and the lower row, where the lower row is towards the distal end of the support frame;
   wherein each hexagonal cell has a plurality of a) straight strut members and b) v-shaped strut members having two arms;
   wherein hexagonal cells in the upper row have a larger cross-sectional area than hexagonal cells in the lower row or the plurality of middle rows;
   wherein, when the prosthetic valve is placed inside a human aortic orifice in crimped condition with the lower row towards the ventricle, the prosthetic valve under fluoroscopy comprises:
      a plurality of light bands; and
      a plurality of dark bands, wherein the plurality of light bands and the dark bands alternate with each other along the length of the support frame;
      wherein at least one edge of a band of the plurality of dark bands or the light bands aligns with the aortic annular plane on placement of the prosthetic valve in orthotopic position of a human aorta.

10. A prosthetic valve with fluoroscopic properties for precise placement of the prosthetic valve in a human aortic orifice, the prosthetic valve comprising:
- a support frame having a distal end, a proximal end and a plurality of adjacently placed rows of hexagonal cells between the distal end and the proximal end, the plurality of the rows comprising an upper row, a lower row and a plurality of middle rows between the upper row and the lower row, where the lower row is towards the distal end of the support frame;
- wherein each hexagonal cell has a plurality of a) straight strut members and b) v-shaped strut members having two arms;
- wherein hexagonal cells in the upper row have a larger cross-sectional area than hexagonal cells in the lower row or the plurality of middle rows;
- wherein when the prosthetic valve is placed inside a human aortic orifice in crimped condition with the lower row towards the ventricle, the prosthetic valve under fluoroscopy comprises:
  - a plurality of light bands; and
  - a plurality of dark bands, wherein the plurality of light bands and the dark bands alternate with each other along the length of the support frame;
  - wherein a band of the plurality of dark bands or the light bands is bisected by the aortic annular plane on placement of the prosthetic valve in orthotopic position of a human aorta.

* * * * *